United States Patent [19]

Hilzinger et al.

[11] 4,192,315
[45] Mar. 11, 1980

[54] CLIP FOR SURGICAL PURPOSES

[75] Inventors: Fritz Hilzinger, Emmingen; Theodor Schwarz, Tuttlingen, both of Fed. Rep. of Germany

[73] Assignee: Aesculap-Werke Aktiengesellschaft vormals Jetter & Scheerer, Tullingen, Fed. Rep. of Germany

[21] Appl. No.: 861,347

[22] Filed: Dec. 16, 1977

[30] Foreign Application Priority Data

Dec. 23, 1976 [DE] Fed. Rep. of Germany ....... 2658478

[51] Int. Cl.² ............................................. A61B 17/12
[52] U.S. Cl. ................................. 128/346; 24/261 C
[58] Field of Search ............... 128/325, 346; 24/261 C

[56] References Cited

U.S. PATENT DOCUMENTS

| 1,741,457 | 12/1929 | Glass | 128/325 |
| 2,653,048 | 9/1953 | Novak | 24/261 C X |
| 3,403,431 | 10/1968 | Butler | 24/261 C |
| 3,827,438 | 8/1974 | Kees | 128/346 |
| 3,868,957 | 3/1975 | Doddington | 128/346 |

FOREIGN PATENT DOCUMENTS 430945  8/1967  Switzerland ............................ 128/346

Primary Examiner—Richard J. Apley
Attorney, Agent, or Firm—Wigman & Cohen

[57] ABSTRACT

This disclosure relates to a clip for surgical purposes comprising a coil spring having at least one loop and a pair of crossing legs. The ends of the legs which extend beyond the crossing point are formed as clamping jaws. Because the portions of the legs adjoining the loop extend generally parallel to one another and the ends of the legs run side-by-side, and because a ring is provided at the crossing point for holding the legs together, the clip can be constructed with such small dimensions that it is particularly advantageously useful for neurosurgical purposes.

1 Claim, 5 Drawing Figures

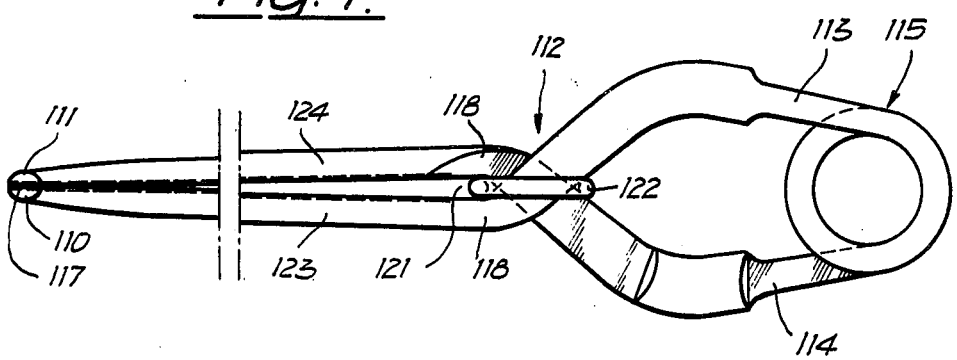
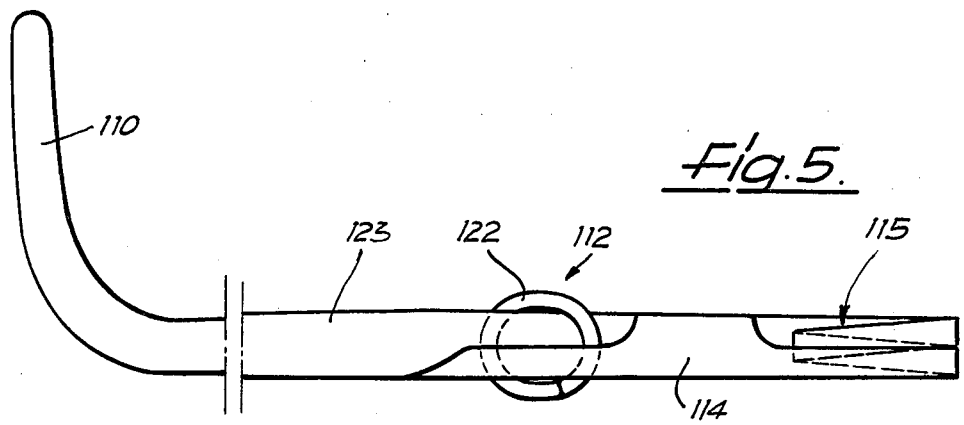

CLIP FOR SURGICAL PURPOSES

BACKGROUND OF THE INVENTION

This invention relates generally to the surgical arts, and more particularly to a vascular clip for surgical purposes, especially for neurosurgical purposes, e.g., for pinching an aneurysm.

U.S. Pat. No. 1,741,457 discloses a surgical vascular clip which has two jaws and a coil spring for pressing the jaws together. The spring includes two bent legs that are joined resiliently to one another by a loop. The loop runs generally parallel to a plane, whereby the legs cross each other at a crossing point and are held together at that point by a connecting member which is slidable along both legs. The jaws are disposed beyond the crossing point at the ends of the legs.

It has been found, however, that the overall size of this prior art clip in relation to its clamping or pinching surfaces is much too large to be used for neurosurgical purposes, especially in the brain. The connecting member, which is slidable along both bent leg ends and holds the leg ends together, is formed as a claw which is bent from a single piece of wire. However, since a vascular clip for neurosurgical purposes should have a total length of no more than approximately 10 mm, it is practically impossible to produce a claw that is small enough to be compatible with a clip of this size. Also, the ends of the claw-shaped connecting piece form little hooks which can be extremely dangerous when using the clip in the area of the brain.

A further disadvantage of the aforementioned prior art vascular clip is that the sliding of the bent leg ends in relation to the claw is greatly impeded. This impediment results from the fact that the claw is slidable along one leg while the other leg extends through the claw generally perpendicularly thereto. Moreover, the portion of the leg which extends through the claw also moves laterally toward the adjoining portion of the first leg during closing or opening of the clip in such a manner that the first leg is pressed into a wedge-shaped angle space formed by the claw and the other leg. The pinching thus caused impedes the movement of both legs relative to one another.

SUMMARY OF THE INVENTION

It should be apparent, therefore, that a need still exists in the art for a vascular clip that overcomes the aforementioned disadvantages of known prior art clips. Accordingly, it is a primary object of this invention to provide a vascular clip for surgical purposes which can be constructed with dimensions small enough so that it can be used for neurosurgical purposes, for example, for use in the brain.

Another object of this invention is to provide a vascular clip comprising two jaws and a coil spring, the portions of the legs immediately adjoining the loop of the coil spring extending generally parallel to one another, so that the portions of the coil spring between the loop and the crossing point of the legs are at a distance from each other which is at most just slightly greater than the diameter of the loop.

A further object of this invention is to provide a vascular clip as described above wherein the ends of the legs which extend beyond the crossing point run next to each other when the clamping jaws thereof lie against one another, thereby permitting the vascular clip to be constructed as small as possible.

Still another object of this invention is to provide a vascular clip as described above wherein an intermediate space remains free directly adjacent to the crossing point of the legs when the jaws lie against one another, and that, in order to hold the legs together at the crossing point, a ring is provided which extends through this intermediate space.

Briefly described, these and other objects of the invention which may become apparent hereinafter are accomplished in accordance with this invention by providing a vascular clip wherein the legs crossing each other are held against one another by a ring in such a way that the ends of the legs cannot move out of their plane of motion during opening and closing of the clip. The ring has no sharp edges or ends which could cause injuries in the area of the operation, e.g., in the brain. Such a ring can also be very easily fitted in the known way. During closing and opening of the vascular clip in accordance with the invention, the ring is in an inclined position of about 45° in relation to both legs, so that no pinching effects are caused by this ring during the opening and closing motions of the vascular clip.

In a preferred embodiment of the invention, the jaws, in their position lying against one another, immediately adjoin the crossing point and their clamping or pinching surfaces are separated from the crossing point by recesses which form the intermediate space through which the ring extends. The length of the vascular clip in accordance with the invention can thus be reduced to a minimum, namely to only about twice the length of the clamping surfaces.

With the above and other objects on the invention in view that may become apparent hereinafter, the nature of the invention will be more clearly understood by reference to the several views illustrated in the accompanying drawings, the following detailed description thereof, and the appended claimed subject matter.

BRIEF DESCRIPTION OF THE DRAWINGS

FIGS. 4 and 5 are greatly enlarged plan and side views, respectively, of a second embodiment of the invention.

DETAILED DESCRIPTION OF PREFERRED EMBODIMENTS

Figure 1:
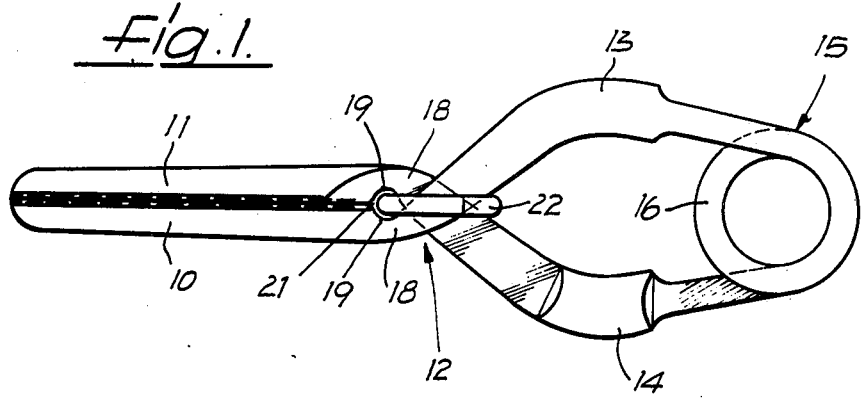
FIGS. 1 and 2 are greatly enlarged plan and side views, respectively, of a first embodiment of the invention.
Figure 2:
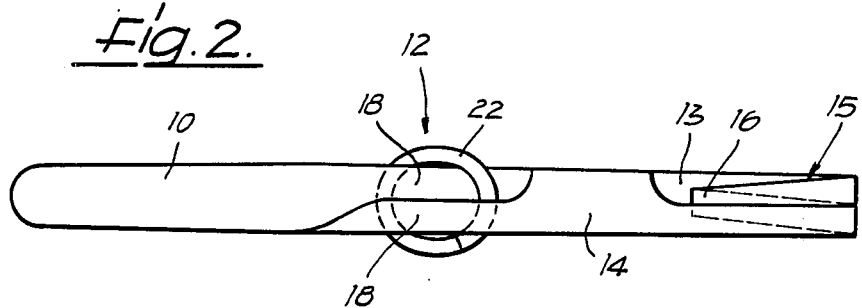
Figure 3:
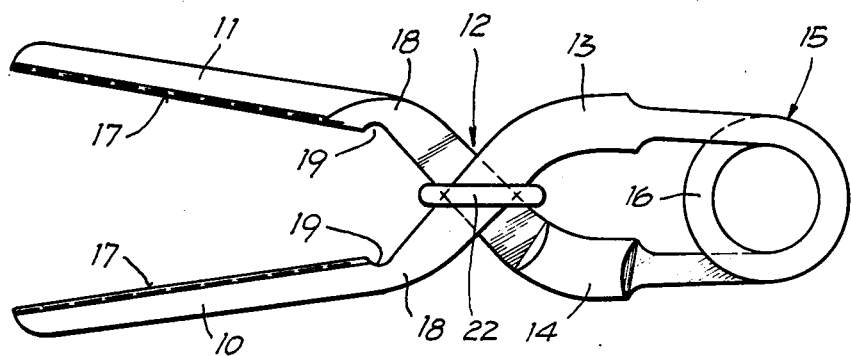
FIG. 3 is a plan view of the opened clip according to the embodiment of FIGS. 1 and 2.

Referring now to the drawings in detail, there is illustrated in FIGS. 1-3 a vascular clip for surgical purposes, especially for neurosurgical purposes, e.g., to pinch shut aneurysms, including two jaws 10, 11 which are formed by the bent ends of two legs 13, 14 of a coil spring 15 crossing each other at a crossing point 12. In the illustrated embodiment the coil spring 15 forms a 360° loop 16 and the jaws 10, 11 extend to a bend 18 of the leg ends. The sides of the jaws 10, 11 which face each other are formed as pinching surfaces 17. Recesses 19 are provided on the ends of the pinching surfaces 17 which adjoin the bend 18 of the leg ends. As seen in FIG. 1 when the pinching surfaces 17 lie against one another the parts of the bent leg ends adjoining the bend 18 are spaced from each other so that there, between the crossing point 12 and the pinching surfaces 17, an opening 21 is formed. A ring 22, encircling the crossing point 12, extend through the opening 21. The ring 22 encircles the crossing legs 13, 14 and holds them together in such a way that they cannot bend out of the plane of motion of the bent leg ends which form the jaws 10, 11 and thereby out of the drawing plane of FIG. 1. However, as seen in FIG. 3, since the ring 22 can freely slide along the crossing legs 13, 14 of the coil spring 15, the opening and closing motion of the clip is not adversely affected.

A second embodiment of the invention is illustrated in FIGS. 4 and 5 and differs from the first embodiment illustrated in FIGS. 1 to 3 in that jaws 110, 111 are provided at the ends of bent leg ends 123, 124 which are so formed that when pinching surfaces 117 of the jaws 110, 111 lie against one another, the parts of the bent leg ends 123, 124 which adjoin the bend 118 are spaced from each other. Consequently, an intermediate space 121 is thus formed through which a ring 122 extends which holds together the crossing legs 113, 114 of the coil spring 115.

As can be seen from the drawings, the rings 22 and 122 may simply be constructed from a bent piece of wire.

Although only preferred embodiments of the invention have been specifically illustrated and described herein, it is to be understood that minor modifications could be made therein without departing from the spirit and scope of the invention as defined in the appended claims.

We claim:

1. A vascular clip having open and closed positions comprising:

two jaws having pinching surfaces;

a coil spring for pressing said pinching surfaces together when the clip is in its closed position;

said coil spring including two legs and at least one coil loop resiliently connecting said legs;

said legs crossing over each other at a crossing point and having end portions immediately adjoining said crossing point;

said jaws being formed by said end portions;

recess means, notched on the inside of each of said end portions, for forming an intermediate space which separates said pinching surfaces from said crossing point in the closed position of said clip; and a ring slidable along and encircling said legs at said crossing point which extends through said intermediate space.

* * * * *